United States Patent [19]

Burress

[11] Patent Number: 4,565,899

[45] Date of Patent: Jan. 21, 1986

[54] IRON OXIDE CATALYSTS CONTAINING COPPER AND ZINC COMPOUNDS AND PROCESS FOR PARA-ETHYLTOLUENE DEHYDROGENATION

[75] Inventor: George T. Burress, Bridgewater, N.J.

[73] Assignee: Mobil Oil Corporation, New York, N.Y.

[21] Appl. No.: 681,968

[22] Filed: Dec. 14, 1984

[51] Int. Cl.$^4$ .................. C07C 2/66; C07C 4/12; C07C 5/32; C07C 5/327

[52] U.S. Cl. .................. 585/445; 585/444; 585/440; 585/443

[58] Field of Search .............. 585/445, 444, 443, 440

[56] References Cited

U.S. PATENT DOCUMENTS

| | | | |
|---|---|---|---|
| 3,360,597 | 12/1967 | Jones et al. | 264/176 |
| 3,364,277 | 1/1968 | Siem | 260/680 |
| 4,134,858 | 1/1979 | Courty | 863/2 |
| 4,152,300 | 5/1979 | Riesser | 899/53 |
| 4,433,186 | 2/1984 | Chu | 585/445 |
| 4,496,662 | 1/1985 | Chu | 585/444 |

FOREIGN PATENT DOCUMENTS

| | | | |
|---|---|---|---|
| 487670 | 10/1952 | Canada | 585/445 |
| 93518 | 11/1983 | European Pat. Off. | 585/445 |
| 892779 | 3/1962 | United Kingdom | 585/445 |

*Primary Examiner*—John Doll
*Assistant Examiner*—Chung K. Pak
*Attorney, Agent, or Firm*—Alexander J. McKillop; Michael G. Gilman; Edward J. Trojnar

[57] ABSTRACT

Para-ethyltoluene dehydrogenation catalyst compositions and processes for using such catalysts are provided. The catalyst compositions comprise a catalytically active iron compound, e.g., iron oxide; a potassium catalyst promoter, e.g., potassium carbonate; an optional chromium compound stabilizer, e.g., chromic oxide, a copper compound, e.g., copper chromite, and a zinc compound, e.g., zinc ferrate. Utilization of particular amounts of zinc ferrate and copper chromite in dehydrogenation catalyst compositions of this type will provide a catalyst especially suitable for promoting the highly selective dehydrogenation of para-ethyltoluene to form para-methylstyrene with excellent conversion.

7 Claims, No Drawings

IRON OXIDE CATALYSTS CONTAINING COPPER AND ZINC COMPOUNDS AND PROCESS FOR PARA-ETHYLTOLUENE DEHYDROGENATION

BACKGROUND OF THE INVENTION

1. Field of the Invention

This invention relates to improved catalysts for the selective dehydrogenation of dialkyl aromatic hydrocarbons to produce alkyl vinyl aromatic hydrocarbons, more particularly to catalysts for the production of para-methylstyrene (PMS) via the dehydrogenation of para-ethyltoluene (PET).

2. The Prior Art

The vinyl benzenes play a particularly important role in the preparation of synthetic plastics and resins. The polymerization of styrenes, for example, to produce polystyrene resins is well known.

Styrene and styrene derivatives are typically produced from ethyl benzene materials by dehydrogenation over solid catalysts in the presence of steam, and at temperatures ranging from 500° to 700° C. The catalysts found to be the most effective for this process are those which are based on potassium oxide (carbonate) promoted, chromium oxide stabilized, iron oxide material. Considerable research has been directed toward attempts to improve the activity and selectivity of this class of catalysts. Any improvement which results in either increasing the selectivity (moles of desired product per mole of reactant reacted) or the conversion (moles of reactant reacted per mole of starting material) without lowering the other is economically attractive since the result is that the yield (moles of desired product produced per mole of reactant) of the product has been increased. Any increase in the numerical value of the yield results in a more efficient operation with more reactant being converted into the desired product. In commercial operations, many of which produce millions of pounds of product per year, a trade-off is frequently necessary between selectivity and conversion. An increase of only 1 or 2 percentage points in the selectivity can result in a substantial savings of starting materials. An increase in conversion can substantially reduce capital expenditure and energy consumption. The trade-off may vary depending on raw materials costs, energy costs, and the age of the plant.

Attempts have been made to improve the conversion effectiveness and selectivity of iron oxide type dehydrogenation catalysts for use in various alkylaromatic dehydrogenation reactions. Riesser; U.S. Pat. No. 4,152,300; issued May 1, 1979, for example, discloses that an improvement in ethylbenzene dehydrogenation catalyst selectivity can be realized by incorporating small amounts of certain metal oxide materials into dehydrogenation catalyst compositions comprising mixtures of iron oxide, potassium oxide, vanadium oxide and, optionally, chromium oxide.

Courty; U.S. Pat. No. 4,134,858; issued Jan. 19, 1979, discloses an iron oxide based dehydrogenation catalyst containing particular amounts of clay to improve the conversion, selectivity and yield of styrene and divinylbenzenes produced by dehydrogenation of ethyl- or diethylbenzene. This '858 patent also notes that oxides of copper, vanadium, zinc, manganese, magnesium, nickel, cobalt, bismuth, tin and antimony can be added to the disclosed dehydrogenation catalysts.

Notwithstanding such attempts to improve iron oxide based dehydrogenation catalysts, there is a continuing need to formulate catalysts of this type which can be used to realize improved conversion, selectivity, and/or yield in the dehydrogenation of other types of alkylaromatic materials such as, for example, in the production of para-methylstyrene from para-ethyltoluene.

Accordingly, it is an object of the present invention to provide an improved iron oxide based dehydrogenation catalyst especially useful for the dehydrogenation of para-ethyltoluene to produce para-methylstyrene.

It is a further object of the present invention to provide a para-ethyltoluene dehydrogenation process employing a catalyst which provides a significant increase in selectivity to production of p-methylstyrene with little or no corresponding drop in para-ethyltoluene conversion.

These and other objectives can be achieved by means of the invention described and claimed herein.

SUMMARY OF THE INVENTION

The present invention relates to an improved dehydrogenation catalyst composition especially useful for the selective dehydrogenation of ethyl benzenes and substituted ethyl benzenes, particularly of para-ethyltoluene to produce para-methylstyrene. Such a catalyst comprises from about 30% to 60% by weight of an iron oxide component, calculated as ferric oxide, from about 13% to 48% by weight of a potassium compound component, calculated as potassium oxide, from about 0% to about 5% by weight of a chromium compound component, calculated as chromic oxide, from about 1% to 10% by weight of a copper compound, and 1 to 10% by weight of a zinc compound.

The present invention also relates to a dehydrogenation process wherein para-ethyltoluene, preferably along with steam, is passed over the catalyst composition at a temperature from about 500° C. to 700° C. with a LHSV of from about 0.3 to 3, to produce para-methylstyrene with high selectivity and excellent conversion.

DETAILED DESCRIPTION OF THE INVENTION

The dehyrogenation catalyst compositions of the present invention contain as an essential catalytic component one or more iron compounds, generally in the form of iron oxide. Many forms of iron oxide can be used in the catalyst compositions of this invention. Typically, iron oxides employed in catalyst preparations of this sort are a synthetically produced, powdered red, red-brown, yellow or black pigment. The red or red-brown pigments are highly pure ferric oxide, while the black pigment is the magnetic form, ferrosoferric oxide ($Fe_3O_4$), which is usually found in the catalyst under various reaction conditions. The yellow iron oxides consist of the monohydrated form of ferric oxide. These oxides are prepared by various methods, e.g., oxidation of iron compounds, roasting, precipitation, calcination, etc. A suitable form of iron compound is the monohydrated yellow iron oxide used in the preparation of catalysts according to U.S. Pat. Nos. 3,360,597, issued Dec. 26, 1967, and 3,364,277; issued Jan. 16, 1968. Particularly suitable are pigment grade red iron oxides of purities exceeding 98% weight. These red oxides have surface areas ranging from 2 to 50 m²/gram and particle sizes from 0.1 to 2 microns. The iron compound is present in the catalyst in either one or a mixture of both of its possible oxidation states, i.e., as ferrous iron or ferric iron or mixtures thereof, as for example, ferrosoferric iron.

The catalyst compositions herein generally comprise from about 30% to 60% by weight, preferably from about 35% to 55% by weight, of iron oxide calculated as ferric oxide. Alternatively stated, the catalyst compositions herein generally comprise from about 21% to 42% by weight, and preferably from about 24% to 39% by weight, of iron oxide, calculated as iron metal.

The dehydrogenation catalyst compositions of the present invention also essentially comprise, as a catalyst promoter, one or more potassium compounds. The potassium promoter material can be added to the catalyst in various forms. For example, it may be added as the oxide, or as other compounds which are convertible, at least in part, under calcination conditions, to the oxides, such as the hydroxides, the carbonates, the bicarbonates, the phosphates, the borates, the acetates, and the like. A particularly preferred potassium compound is potassium carbonate. The potassium compound is generally present in the catalyst as a potassium oxide, a potassium carbonate or a mixture thereof. High carbon dioxide partial pressures in the reaction gases will favor high carbonate to oxide ratios and vice versa within the potassium component.

The catalyst compositions herein generally comprise from about 13% to 48% by weight, and preferably from about 27% to 41% by weight, of potassium promoter compound, calculated as potassium oxide. It is preferred that the molar ratio of the potassium oxide to the ferric oxide be from 0.8:1 to 1.6 to 1.

An optional, but preferred third component of the present catalyst composition is a chromium compound which serves as a stabilizer for the active catalytic components. Chromium compounds have, in fact, typically been added to alkali-promoted iron oxide catalysts to extend their life. Chromium, as used in the compositions of this invention, can be added to the catalyst in the form of a chromium oxide or in the form of chromium compounds which decompose upon calcination to chromium oxides, as for example, chromium nitrates, hydroxides, acetates, and the like. Chromium can also be added in the form of alkali metal chromates. If potassium chromates are used, such materials can, of course, also contribute to the requisite concentration of potassium essentially present in the dehydrogenation catalyst compositions as hereinbefore discussed.

Thus, the catalyst compositions herein can comprise from about 0% to about 5% by weight, and preferably from about 1% to 4% by weight chromium compound, calculated as chromic oxide. Alternatively stated, the present composition can comprise from about 0% to 3.5% by weight, preferably from about 1.4% to 2.8% by weight, of a chromium oxide calculated as chromium metal.

In accordance with the present invention, the dehydrogenation catalyst compositions containing iron, potassium and optional chromium compounds, as described, also essentially contain particular selected amounts of a copper compound and a zinc compound. The copper compound is preferably a copper oxide and most preferably copper chromite ($CuCr_2O_4$). The zinc compound is preferably an oxide, and most preferably zinc ferrate ($ZnFe_2O_4$). The proportions of the copper and zinc compounds can vary considerably. Copper chromite and zinc ferrate are advantageously used in amounts of 1 to 10 weight percent, preferably 1 to 5 weight percent.

In addition to the foregoing materials, the catalyst compositions of the present invention can optionally contain a wide variety of materials suitable for altering, adjusting or modifying the catalytic and/or physical properties of such compositions. Materials, for example, which can act as stabilizers, activators, and promoters for dehydrogenation catalysts of the type herein contemplated include, cobalt, cadmium, aluminum, nickel, cesium, and rare earths. Such additives can be incorporated in various forms including their elemental form or in the form of their oxides. If employed, such stabilizers, activators and/or promoters generally comprise from about 1% to 15% by weight of the catalyst compositions herein.

It should be noted that the compositions of the present invention need not contain materials such as potassium aluminosilicate, e.g., kaliophyllite, in order to enhance catalyst activity and/or selectivity to production of p-methylstyrene products. The catalysts of the present invention, in fact, can be maintained substantially free of clays or clay-like material without adversely affecting catalyst dehydrogenation activity or p-methylstyrene selectivity when used to promote dehydrogenation of p-ethyltoluene.

The physical strength of the catalyst compositions of the present invention can be improved, if desired, by adding any of a variety of optional insoluble binding agents. Binding agents can include, for example, calcium aluminate and portland cement. The density of the catalyst compositions herein can likewise be modified by the addition of various filler substances, for example, combustible materials such as sawdust, carbon, wood flour, etc. Such materials can be added to the compositions during preparation and thereafter burned out after the catalyst pellets have been formed. Other porosity promoting aids include graphite and aqueous solutions of methylcelluose, which also facilitate extrusion of catalyst pellets as hereinafter described. If employed, binders and other fillers generally can comprise up to about 20% by weight of the catalyst composition.

The catalyst compositions of the present invention are in general prepared by admixing the essential and desired optional components as hereinbefore described and by thereafter drying and optionally calcining the resulting mixture. Calcination temperatures can thus range from about 100° C. to 600° C., preferably from about 150° C. to 550° C.

The compounds of the catalyst compositions herein can be admixed in various ways. One method comprises ballmilling together a mixture of the desired oxides and/or compounds decomposable upon calcination to oxides, adding a small amount of water, and extruding the paste formed to produce small pellets, which are then dried and calcined. Another method is to dissolve the components together, spray dry these components to form a resulting powder, calcine the powder into the resultant oxides, and then add sufficient water to form a paste which is extruded into pellets, dried and calcined. Another procedure involves precipitating those materials which are precipitatable, such as iron and chromium, as the resultant hydroxides, partially dewatering the resultant precipitate, adding soluble salts of the other desired metals, and then subsequently extruding, drying and calcining the resulting pellets. A preferred method involves dry-blend powdering of oxides and/or compounds decomposable upon calcination to the oxides, adding water, optionally containing dissolved therein soluble compounds decomposable upon calcination to the oxides, then mixing and/or mulling the resultant paste, pelletizing the mixture, subsequently substantially drying at a temperature from about 50° C. to about 300° C., followed by calcining the pellets to form the final product. The drying and calcining could be carried out stepwise in the same furnace by suitable programming of the furnace temperature. Alternatively, water-insoluble dry powders of oxides and/or compounds decomposable upon calcination to the oxides are dry-mixed, and the balance of the other materials needed are dissolved in water and the resultant solution is used to form the paste with the dry powders. There are many variations of the mixing of dry powders, water and water soluble compounds that give equivalent results and fall within the scope of this invention.

The catalysts of this invention are especially effective in promoting the dehydrogenation of para-ethyltoluene to selectively produce para-methylstyrene. Such a dehydrogenation reaction is usually carried out at reaction temperatures of about 500° C.–700° C. However, higher or lower temperatures may be used without departing from the scope of this invention. The use of atmospheric, sub-atmospheric, or super-atmospheric pressure is suitable. However, it is preferable to operate at as low a pressure as is feasible, and atmospheric or sub-atmospheric pressure is preferred. The process of the invention may be carried out in batch, semi-continuous, or continuous operation, with continuous operation being preferred. The catalyst is employed in the form of a fixed bed, or in fluidized or suspended form. It is preferable to utilize a fixed bed. The reaction may be carried out in single stage reactors or by staging in series reactors. The reactors may be of various designs, e.g., downflow reactors, radial reactors, etc.

With the use of the catalyst of this invention, it is desirable to add steam to the reactant feed to aid in the removal of carbonaceous residues from the catalyst. The reaction feed generally contains from 2–30 moles of steam for every mole of organic feed. Catalysts having higher potassium contents are usually employed at lower steam to feed ratios. Steam to feed weight ratios of from about 1:1 to about 5:1 are desirable. Good results are obtained with steam to feed ratios of about 1.6:1 to about 4:1.

The contact time of the reactant-containing gas with the catalyst is usually defined in terms of liquid-hourly-space velocity (volume of liquid hydrocarbon reactant per volume of catalyst per hour, i.e., LHSV). The LHSV of the organic reactants according to this invention may vary from about 0.3 to 3 and is preferably adjusted within this range to effect the degree of conversion desired for the particular feed in question.

The catalysts of the present invention and their use will be further described by the following illustrative examples which are provided for illustration and are not to be construed as limiting the invention. It should be noted that advantages resulting from increases of selectivity and/or conversion of only one or two percentage points are extremely significant in a commerical process which may produce many hundreds of thousand pounds of product a day.

EXAMPLE

A p-ethyltoluene dehydrogenation catalyst with the following composition was prepared.

|  | wt % |
|---|---|
| α-Fe$_2$O$_3$ | 41.8 |

-continued

|  | wt % |
|---|---|
| K$_2$CO$_3$ | 49.2 |
| Cr$_2$O$_3$ | 2.7 |
| CuCr$_2$O$_4$ | 2.7 |
| ZnFe$_2$O$_4$ | 3.6 |
|  | 100.0 | p-ethyltoluene and steam were fed over this catalyst to obtain p-methylstyrene. Following are the conditions and results obtained.

| Temp., °C. | H$_2$O/PET wt/wt | LHSV | PET mole % Conversion | PMS mole % Selectivity |
|---|---|---|---|---|
| 620 | 2/1 | 1 | 66.0 | 90.0 |
| 620 | 1.85/1 | 1 | 62.0 | 90.5 |
| 620 | 1.85/1 | 1.25 | 62.0 | 91.0 |
| 625 | 1.85/1 | 1.25 | 65.0 | 90.0 |

COMPARATIVE EXAMPLE

A catalyst prepared as in the Example above but without the added CuCr$_2$O$_4$ and ZnFe$_2$O$_4$ at 620° C. and 2/1 H$_2$O/PET gave only 58.0 mole % conversion of PET with a PMS selectivity of about 89.0%.

What is claimed is:

1. A process for the dehydrogenation of para-ethyltoluene to selectively form para-methylstyrene, said process comprising contacting para-ethyltoluene under dehydrogenation reaction conditions with a catalyst composition comprising:
   a. from about 30% to 60% by weight of iron oxide, calculated as ferric oxide;
   b. from about 13% to 48% by weight of potassium compound, calculated as potassium oxide;
   c. from about 0% to about 5% of chromium compound, calculated as chromic oxide;
   d. from about 1% to 10% by weight of copper chromite; and
   e. from 1% to 10% by weight of zinc ferrate.

2. A process in accordance with claim 1 wherein said dehydrogenation conditions include a temperature of from about 500° C. to 700° C., and a liquid hourly space velocity for para-ethyltoluene of from about 0.3 to 3.

3. A process in accordance with claim 2 wherein
   a. the iron oxide comprises from about 35% to 55% by weight of the catalyst composition;
   b. the potassium compound comprises from about 27% to 41% by weight of the catalyst composition;
   c. the chromium compound comprises from about 1% to 4% by weight of the catalyst composition;
   d. the copper chromite comprises from about 2% to 5% by weight of the catalyst composition; and
   e. the zinc ferrate comprises 2% to 5% by weight of the catalyst composition.

4. A process in accordance with claim 3 wherein para-ethlytoluene is contacted with said catalyst in the presence of steam and wherein the weight ratio of steam to para-ethyltoluene ranges from about 1:1 to 5:1.

5. A process in accordance with claim 4 wherein said catalyst composition is substantially free of clay material.

6. A process in accordance with claim 1 wherein said catalyst composition additionally contains up to about 20% by weight of an insoluble binder/filler component.

7. The process of claim 1 in which the yield of para-methylstyrene (conversion multiplied by selectivity) is greater than obtained under identical conditions in which the catalyst does not contain the added CuCr$_2$O$_4$ and ZnFe$_2$O$_4$.

* * * * *